(12) United States Patent
Muller et al.

(10) Patent No.: US 8,958,527 B2
(45) Date of Patent: Feb. 17, 2015

(54) METHOD FOR ACQUIRING MORPHOLOGY OF A BREAST

(75) Inventors: Serge Muller, Guyancourt (FR); Sylvie Puong, Paris (FR); Ann-Katherine Carton, Issy-les-Moulineaux (FR); Razvan Iordache, Paris (FR)

(73) Assignee: General Electric Company, Schenectady, NY (US)

( * ) Notice: Subject to any disclaimer, the term of this patent is extended or adjusted under 35 U.S.C. 154(b) by 222 days.

(21) Appl. No.: 13/397,211

(22) Filed: Feb. 15, 2012

(65) Prior Publication Data

US 2013/0044861 A1    Feb. 21, 2013

(30) Foreign Application Priority Data

Feb. 15, 2011  (FR) ...................... 11 51227

(51) Int. Cl.
*A61B 6/00* (2006.01)
*A61B 6/02* (2006.01)
*A61B 6/04* (2006.01)

(52) U.S. Cl.
CPC .................. *A61B 6/025* (2013.01); *A61B 6/482* (2013.01); *A61B 6/502* (2013.01); *A61B 6/0414* (2013.01); *A61B 6/481* (2013.01)
USPC .............................................. 378/62; 378/37

(58) Field of Classification Search
CPC .............................. A61B 6/025; A61B 6/482
USPC ...................................................... 378/37, 62
See application file for complete search history.

(56) References Cited

U.S. PATENT DOCUMENTS

| | | | |
|---|---|---|---|
| 2006/0269040 A1* | 11/2006 | Mertelmeier | 378/37 |
| 2006/0269041 A1 | 11/2006 | Mertelmeier | |
| 2009/0262893 A1* | 10/2009 | Stewart et al. | 378/62 |

FOREIGN PATENT DOCUMENTS

| | | |
|---|---|---|
| DE | 102005022899 A1 | 11/2006 |
| EP | 1759637 A2 | 3/2007 |
| EP | 2213234 A1 | 8/2010 |
| FR | 2881338 A1 | 8/2006 |

OTHER PUBLICATIONS

Lewin; Isaacs; Vance; , Larke; : Dual-energy contrast-enhanced digital subtraction mammography: Feasibility. Radiology 2003; 264:261-268.

(Continued)

*Primary Examiner* — Hoon Song
*Assistant Examiner* — Danielle Fox
(74) *Attorney, Agent, or Firm* — GE Global Patent Operation; Marc A. Vivenzio

(57) ABSTRACT

An imaging method performed by a device comprising an X-ray emitting source, a receiver positioned facing the source, and a support on which a subject or organ to be imaged is positioned, the method comprises defining a first set of orientations of the source and a second set of orientations of the source, and acquiring images at the defined orientations of the source, wherein if the first set of orientations comprises an orientation that the second set of orientations does not comprise, only one image is acquired at the orientation, and if both the first set of orientations and the second set of orientations comprise the same orientation, at least two images are acquired at distinct acquisition parameters at the orientation.

9 Claims, 2 Drawing Sheets

(56) References Cited

OTHER PUBLICATIONS

Puong; Bouchevreau; Patoureaux; Iordache; Muller : Dual-energy contrast enhanced digital mammography using a new approach for breast tissue canceling. In: Hsieh J, Flynn MJ, eds. Medical Imaging 2007: Physics of Medical Imaging. San Diego: SPIE, 2007.

Puong; Patoureaux; Iordache; Muller : Dual-energy contrast enhanced digital breast tomosynthesis: concept, method, and evaluation on phantoms. In: Hsieh J, Flynn MJ, eds. Medical Imaging 2007: Physics of Medical Imaging. San Diego: SPIE, 2007.

Carton; Currivan; Conant; Maidment: Temporal Subtraction Versus Dual-Energy Contrast-Enhanced Digital Breast Tomosynthesis: A Pilot Study. Lecture Notes in Computer Science 2008; 5116:166-173.

Carton AK, Gavenonis SC, Currivan JA, Conant EF, Schnall MD, Maidment ADA: Dual-Energy Contrast-Enhanced Digital Breast Tomosynthesis—A Feasibility Study. Brit. J. Radiol. 2010.

Search Report and Written Opinion from FR Application No. 1151227 dated Oct. 3, 2011.

Search Report from CN Application No. 2012100417631 dated Dec. 10, 2013.

* cited by examiner

METHOD FOR ACQUIRING MORPHOLOGY OF A BREAST

BACKGROUND OF THE INVENTION

1. Field of the Invention

Embodiments of the present invention relate to the field of medical imaging with X-rays and, more particularly, to tomosynthesis methods.

2. Description of the Prior Art

Conventional digital imaging methods apply different techniques, such as tomosynthesis and the production of double or triple energy images, which may be combined with an injection of a contrast product.

X-ray emission is characterized by an emission spectrum (or energy spectrum) and a number of emitted photons. The emission spectrum is defined by the materials in which the X-ray emission tube and the filter positioned at the output of this tube are made as well as the maximum energy of the spectrum.

Tomosynthesis is an alternative of tomography in which a limited number of radiographic projections of an organ to be imaged of a patient are acquired at different angles with respect to the patient. All of these projections acquired at different angles are then processed by means of a reconstruction algorithm adapted for obtaining three-dimensional information on the organ of the patient. This three-dimensional information may be displayed as a three-dimensional representation. The application of tomosynthesis to imaging of the breast is also known as Digital Breast Tomosynthesis ("DBT").

Double or triple energy imaging consists of acquiring several images of this organ from the same orientation with different energy spectra and combining these images by performing subtraction to obtain a model that only has one of the materials which had entered the composition of the targeted organ to be imaged.

Double or triple energy imaging may be combined with the preliminary injection of a contrast product (such as iodine) in the subject or the targeted organ to be imaged. The acquired images are combined by performing a subtraction in order to obtain a model which only shows the contrast product injected into the subject or targeted organ to be imaged. Application of double energy imaging with injection of a contrast product into the breast is known under the designation of Contrast Enhanced Spectral Mammography ("CESM").

The contrast product used may have discontinuities which form local maxima in its radiological attenuation spectrum. These discontinuities, in particular the one known as k-edge, are used for selecting the emission spectra.

In multi-energy methods, a so-called "high energy" image is produced typically with "high energy" acquisition parameters, and a so-called "low energy" image, with "low energy" acquisition parameters.

The "high energy" acquisition parameters correspond to an emission spectrum having a maximum energy which is higher than the k-edge of the contrast product used, while the low acquisition parameters correspond to an emission spectrum having a maximum energy which is lower than the k-edge of the contrast product used.

As an example, iodine has such a discontinuity at 33.5 keV (the k-edge of iodine).

The combination of both of these methods is known, i.e. performing several acquisitions with different energy spectra for each of the orientations used during a tomosynthesis method, such a method being called Contrast Enhanced Digital Breast Tomosynthesis ("CE-DBT").

This CE-DBT method consists of performing a subtraction between the images acquired according to the same orientations with different energy spectra and modeling by means of a reconstruction algorithm to obtain a model of the contrast product volume in the organ to be imaged, typically a breast.

This method however has disadvantages. Indeed, the systematic acquisition of several images for each of the orientations involves a relatively long total acquisition time, approximately thirty seconds, which is far from the common assumption in imaging methods which estimates the acquisition time to be zero or negligible.

However, in the present case, the relatively long acquisition time may involve a displacement of the contrast product, which is not desirable. Further, the longer the acquisition time, the more likely it is that the patient will move, which would decrease the quality of the acquisition and of the resulting model.

Furthermore, the total X-ray dose is distributed among the acquired images, which are numerous, which results in a low dose for each image and therefore significant noise. However, the known reconstruction and subtraction algorithms amplify the noise present in the acquired images.

Therefore, the reconstructed contrast product volume by means of this CE-DBT method exhibits a high degree of noise.

BRIEF SUMMARY OF THE INVENTION

In accordance with an embodiment of the present invention, there is provided an imaging method performed by a device comprising an X-ray emitting source, a receiver positioned facing the source, and a support on which a subject or organ to be imaged is positioned, the method comprises defining a first set of orientations of the source and a second set of orientations of the source, and acquiring images at the defined orientations of the source, wherein if the first set of orientations comprises an orientation that the second set of orientations does not comprise, only one image is acquired at the orientation, and if both the first set of orientations and the second set of orientations comprise the same orientation, at least two images are acquired at distinct acquisition parameters at the orientation.

In accordance with an embodiment of the present invention, there is provided an imaging system, the system comprises an X-ray emitting source, a receiver positioned facing the source, a support on which a subject or organ to be imaged is positioned, and an actuator configured to vary the orientation of the source with respect to the support, to allow displacement of the source according to a first set of orientations and a second set of orientations, and to control the acquisition of images according to distinct energy levels, wherein if the first set of orientations comprises an orientation that the second set of orientations does not comprise, only one image is acquired at the orientation, and if both the first set of orientations and the second set of orientations comprise the same orientation, at least two images are acquired at distinct acquisition parameters at the orientation.

BRIEF DESCRIPTION OF THE DRAWINGS

Other features, objects and advantages of the invention will become apparent from the following description, which is purely an illustration and not a limitation, and which should be read with reference to the appended drawings, wherein.

DETAILED DESCRIPTION OF THE INVENTION

Embodiments of the present invention propose solutions which do not have the disadvantages in the prior art.

Figure 1:
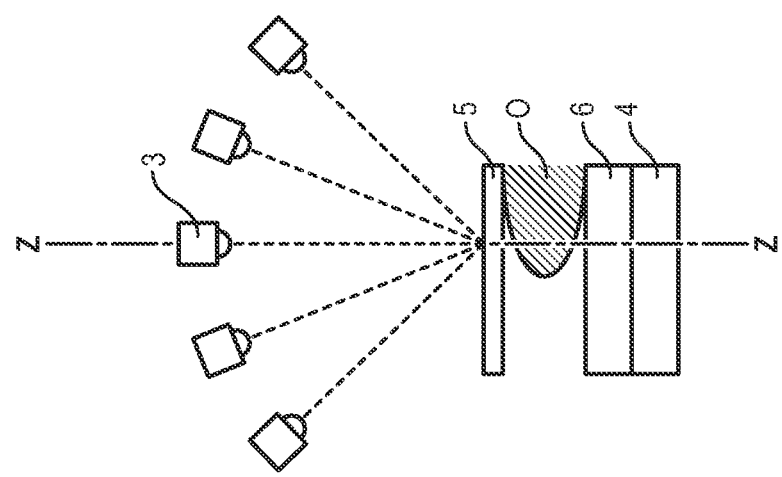
FIG. 1 shows a partial view of a medical imaging system.

FIG. 1 shows a partial view of a medical imaging system, comprising an X-ray emitting source 3, a receiver 4 positioned facing the source 3, and a compression plate 5. A subject or organ to be imaged O, typically the breast of a subject, is positioned on a support 6 and is compressed and held in position by the compression plate 5.

The direction Z-Z perpendicular to the receiver 4, typically the vertical direction with respect to which the subsequent orientations will be located, is illustrated in FIG. 1.

FIG. 1 illustrates the source 3 positioned in five orientations regularly distributed around the direction Z-Z; a central orientation corresponding to the axis Z-Z, and two orientations on each side of this axis, substantially parallel with respect to Z-Z.

These orientations are typically used for producing several images of the subject or organ to be imaged O within the scope of a tomosynthesis method.

Figure 2:
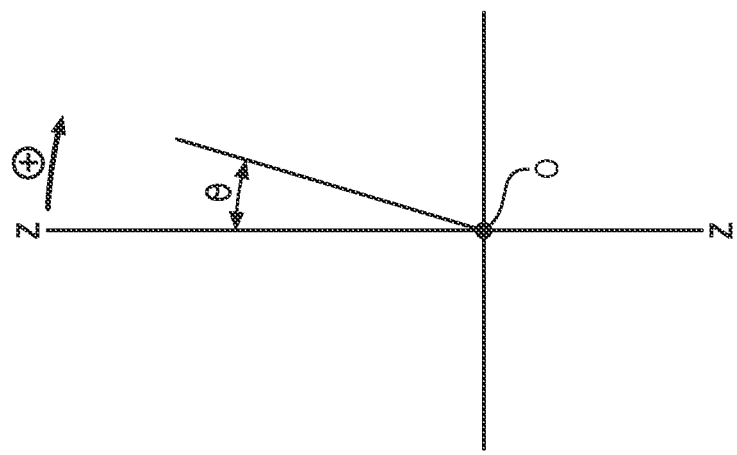
FIG. 2 illustrates a simplified geometrical model of this system.

FIG. 2 illustrates a model in which the subject or organ to be imaged O is assimilated to a point, and wherein an angle $\theta$ is located with respect to the Z-Z axis, this angle $\theta$ designating the orientation of the emitting source with respect to the Z-Z axis for the emission of X-rays.

Embodiments of the present invention consist of combining a tomosynthesis method with multi-energy acquisitions, typically with preliminary injection of a contrast product, wherein the multi-energy acquisitions being performed at orientations distinct from the orientations at which the images are acquired by the tomosynthesis method.

More specifically, a first acquisition of images within the scope of a tomosynthesis method according to a first set of orientations delimited by two extreme orientations, which will be described as a "first acquisition"; and a second acquisition of images within the scope of the multi-energy method according to a second set of orientations distinct from the first set of orientations, which will be described as a "second acquisition" are performed. In an embodiment, the second set of orientations are delimited by two other extreme orientations strictly comprised between both of the extreme orientations of the first set of orientations and comprising at least one orientation; in another embodiment, the second set of orientations can be delimited by two other extreme orientations that have a larger angle $\theta$ than the angle of the extreme orientations of the first set of orientations.

Thus, the first set of orientations and the second set of orientations are not equal.

For example, if the orientations of the first set of orientations are comprised between −30° and +30° with respect to the Z-Z axis, such as {−30°, −15°, 0°, +15°, +30°}, a second set of orientations may be: {−20°, 0°, +20°}; {−15°, 0°, +15°]; {−20°, −10°, 0°, +10°, +20°}; or {−35°, −15°, 0°, +15°, +35°}.

The examples of the second set of orientations given earlier are all centered on the Z-Z axis, and all have an orientation at 0°. However, having an orientation at 0° is not required.

The second set of orientations typically comprises a number of orientations less than the number of orientations contained in the first set of orientations, so the time for the second acquisition may actually be reduced.

More generally, for a first set of orientations comprised in a set [−X°; +X°], the second set of orientations is typically comprised in the set [−X; +X°], wherein X is an angle typically between 10° and 90°.

According to another embodiment, the orientations of the first and of the second set of orientations are asymmetrically distributed with respect to Z-Z; the first set of orientations may then be comprised in a set [X°; 0°], or in a set [X°; Y°] with X being distinct from Y, the second set of orientations then being comprised in the set [X°; 0°] and [X°; Y°], respectively.

In another embodiment, tomosynthesis images can also be acquired asymmetrically with the respect to the Z-Z axis.

The images acquired according to the orientations of the first set of orientations are acquired at a first set of emission parameters, which may be constant on all the orientations of the first set of orientations, or vary depending on the different orientations.

The multi-energy method may be performed in different ways: by combining images acquired according to the first set of orientations and images acquired according to the second set of orientations when both of these sets have common orientations; and/or by combining several images acquired according to a same orientation of the second set of orientations at different emission parameters.

Several alternatives are therefore distinguished.

According to a one embodiment, the images acquired by the tomosynthesis method and those acquired by the multi-energy method are distinct; each of the orientations of the second set of orientations is therefore used for acquiring several images having distinct acquisition parameters in order to achieve multi-energy acquisition.

According to another embodiment, the images acquired by the tomosynthesis method at orientations common to the first and second set of orientations are exploited within the scope of the multi-energy acquisition.

For example, in the following particular case: first set of orientations, {−30°, −15°, 0°, +15°, +30°}, and second set of orientations, {−15°, 0°, +15°}. A single image acquired according to each of the orientations of the second set of orientations is sufficient for performing a double energy method by combining this image with the corresponding image produced according to the first set of orientations, provided that the spectrum of the X-rays emitted during the acquisition according to the second set orientations is distinct, typically by having a greater maximum energy value than the maximum energy value of the spectrum of the emitted X-rays for performing the acquisition according to the corresponding orientation of the first set of orientations.

A combination of these embodiments may also be contemplated, wherein, for the orientations common to the first and second orientations, the multi-energy method is performed by exploiting the images acquired during the first acquisition and by combining them with those of the second acquisition; for orientations only belonging to the second set of orientations and not to the first, the multi-energy method is performed by exploiting the images acquired during the second acquisition, each of the orientations only belonging to the second set of orientations and not to the first, being therefore necessarily used for producing several images acquired at distinct spectra.

This particular embodiment is expressed by the non-redundancy of acquisitions for orientations common to both sets of orientations.

The tomographic reconstruction of the volume of the subject or organ to be imaged is achieved from images acquired according to the first set of orientations, and/or images acquired according to the second set of orientations.

The images acquired according to the first set of orientations are typically sufficient for achieving tomographic reconstruction of the volume of the subject or organ to be imaged, but may however be associated with all or part of the images acquired according to the second set of orientations, notably in the case when the second set of orientations comprises orientations which are not present in the first set of orientations.

Alternatively, tomographic reconstruction may be achieved from all or part of the images acquired according to the second set of orientations.

In one embodiment, as an example, the first set of orientations are equal to $\{-30°, -15°, 0°, +15°, +30°\}$ and the second set of orientations are equal to $\{-25°, -15°, 0°, +15°, +25°\}$. Images are acquired during a first acquisition, wherein one image according to each of the orientations of the first set of orientations is acquired. During a second acquisition, two images for the orientations $-25°$ and $+25°$, and a single image for each of the orientations $-15°$, $0°$ and $+15°$ are acquired, which will be combined with the corresponding image acquired during the first acquisition.

The number of images acquired during the second acquisition depends on the multi-energy method and typically varies between one and three images for each orientation, depending on the embodiment.

The images acquired according to the first set of orientations are acquired at an emission spectrum according to a first set of spectra, and the images acquired according to the second set of orientations are acquired at an emission spectrum according to a second set of spectra, the maximum energy of each of the emission spectra of the first set of spectra being typically lower or equal to the maximum energy of each of the emission spectra of the second set of spectra.

The acquisition parameters, at which the images of the first set are acquired, are typically equal or variable depending on the orientations.

For example, for an equal distribution in the case of a first acquisition performed with a total dose equal to 1 and comprising n images according to distinct orientations (with n being a natural integer), each of the acquired images will be acquired via emission of X-rays at a dose equal to 1/n.

For a variable distribution depending on the orientations, it is possible to define for five distinct orientations doses of the type, for example $\{1/10; 2/10; 4/10; 2/10; 1/10\}$, the central orientation typically corresponding to the Z-Z axis being typically the one for which the dose is the highest.

The acquisition parameters of the second set of acquisition parameters are typically greater than or equal to the acquisition parameters of the first set of acquisition parameters, i.e. the maximum intensity of the emission spectra of the second set of acquisition parameters is greater than or equal to the maximum intensity of the emission spectra of the first set of acquisition parameters.

Performing the multi-energy method requires at least two images acquired at different acquisition parameters for each of the orientations; several alternatives may therefore be contemplated.

According to an embodiment, an image with first acquisition parameters I1 for a given orientation is acquired, and then a second image with second acquisition parameters I2 for this same orientation is acquired, wherein I2≠I1. This acquisition being repeated for the different orientations of the second set of orientations, and double energy modeling is then achieved from both of these images by suitable means of reconstruction algorithm.

In the case of a triple or greater multiple energy method, additional images are acquired at the same orientations, at acquisition parameters distinct from the previous acquisition parameters and a reconstruction algorithm suitable for triple energy or greater multiple energy is used.

According to another embodiment, the images of the first acquisition are exploited for performing the multi-energy method, during the second acquisition, it is therefore possible to acquire a more reduced number of images according to the orientations common to the first and to the second set of orientations.

For example, if a double energy method is performed at the orientations common to the first and to the second set of orientations, it is possible to merely acquire a single image during the second acquisition, and to associate it with the image acquired at the same orientation during the first acquisition.

It will easily be understood that for a triple energy method, an additional image is acquired for each of these orientations and a suitable algorithm is used.

In one embodiment, a first set of orientations $\{\sigma_{1,i=1}^{N}\}$, a second set of orientations $\{\sigma_{2,i=1}^{M}\}$, a first set of acquisition parameters $\{E_{1,j=1}^{N}\}$, and a second set of acquisition parameters $\{E_{2,i=1,k}^{M}\}$ are defined, wherein N and M are natural integers greater than 1, such that N>M, respectively corresponding to the number of orientations of the first and of the second set, k being a non-zero natural integer, and while respectively designating $\sigma_{1,min}$, $\sigma_{1,max}$, $\sigma_{2,min}$ and $\sigma_{2,max}$ as the extreme orientations of the first and of the second set of orientations, while $\sigma_{1,min}<\sigma_{2,min}$ and $\sigma_{1,max}>\sigma_{2,max}$. The acquisition parameters are defined by an emission spectrum and by a number of emitted photons.

For the values of i such that $\sigma_{1,j}\neq\sigma_{2,j}$, an acquisition is performed according to the orientations $\sigma_{1,j}$ at acquisition parameters $E_{1,i}$; according to the orientations $\sigma_{2,j}$ at a number k of distinct acquisition parameters $E_{1,j,k}$, with k being a natural integer >1.

For the values of I such that $\sigma_{1,i}=\sigma_{2,j}$, an acquisition according to each of these orientations $\sigma_{1,i}$ at acquisition parameters $E_{1,i}$ and at least one acquisition according to each of the orientations $\sigma_{1,i}$ at acquisition parameters $E_{2,i,k}$ are performed.

Figure 3:
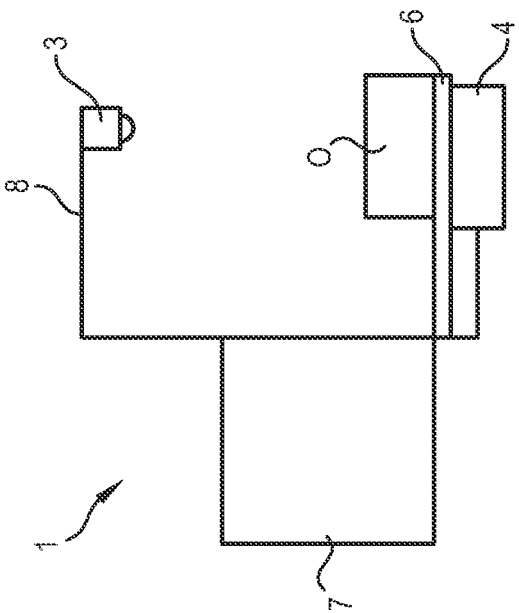
FIG. 3 illustrates a particular example of the method according to an embodiment of the present invention.

FIG. 3 illustrates a particular example, in which a double energy method is performed. By defining a first ordered set of orientations $\{\sigma_{1,1}, \sigma_{1,2}, \sigma_{1,3}\}$ and a second ordered set of orientations $\{\sigma_{2,1}, \sigma_{2,2}, \sigma_{2,3}\}$ such that $\sigma_{1,1}<\sigma_{2,1}$, $\sigma_{2,3}<\sigma_{1,3}$ and $\sigma_{1,2}=\sigma_{2,2}$, an acquisition of images is performed according to each of the orientations $\sigma_{1,1}$, $\sigma_{1,2}$ and $\sigma_{1,3}$, and at each respective acquisition parameters $E_{1,1}$, $E_{1,2}$ and $E_{1,3}$. According to the orientation $\sigma_{2,1}$, two images are acquired at the respective distinct acquisition parameters $E_{2,1,1}$ and $E_{2,1,2}$; according to the orientation $\sigma_{2,3}$ two images are acquired at the respective distinct acquisition parameters $E_{2,3,1}$ and $E_{2,3,2}$; according to the orientation $\sigma_{1,2}=\sigma_{2,2}$, one image is acquired at acquisition parameters $E_{2,2,2}$, and or two images are acquired at the respective acquisition parameters $E_{2,2,1}$ and $E_{2,2,2}$.

In the case when only one image is acquired at the acquisition parameters $E_{2,2,2}$, the double energy method is performed from the image acquired for the orientation $\sigma_{1,2}=\sigma_{2,2}$ at the acquisition parameter $E_{1,2}$ combined with the image acquired at the acquisition parameters $E_{2,2,2}$, both of these acquisition parameters being distinct.

In the case when two images are acquired at distinct respective acquisition parameters $E_{2,2,1}$ and $E_{2,2,2}$, the double energy method is performed (obtaining the modeling of the contrast product volume) from both of these images, the image acquired at acquisition parameters $E_{1,2}$ being, is used for performing the tomosynthesis method (obtaining the modeling of the internal volume of the subject or organ to be imaged O).

The acquisition of the images at different acquisition parameters and at different orientations may be performed according to several distinct sequences. In one embodiment, a single displacement of the X-ray emitting source is performed between two extreme orientations $\sigma_{1,1}$ and $\sigma_{1,3}$ of the first set of orientations, the acquisitions at the different acquisition parameters all being performed during this single passage. In another embodiment a first displacement of the X-ray emitting source is performed between the first and the second extreme orientation of the first set of orientations, for example $\sigma_{1,1}$ to $\sigma_{1,3}$ in the example illustrated in FIG. 3, during which a single acquisition is performed for each of the orientations of the first set of orientations. A second displacement of the X-ray emitting source from the second to the first extreme orientation of the second set of orientations (or vice versa) is then performed, for example from $\sigma_{2,3}$ to $\sigma_{2,1}$ in the example illustrated in FIG. 3, during which at least one acquisition is performed for each of the orientations of the second set of orientations.

According to an embodiment of the present invention, it is possible to obtain complete modeling of a subject or organ to be imaged O by minimizing the acquisition time, therefore the contrast product injected into the subject or organ to be imaged O would have a lower possibility of moving during the acquisition of the different images.

Further, embodiments of the present invention reduce the number of image acquisitions as compared with methods such as CE-DBT, which reduces the noise present in the images and in the reconstructed volumes. Indeed, with the reduced number of image acquisitions, a larger dose may be allocated for each dose used by an image acquisition, as compared with the CE-DBT method.

With the acquisition it is thus possible to achieve two types of distinct representations: a tomosynthesis representation by tomographic reconstruction, and a double or multi-energy representation by image processing.

These representations are displayed so that the user may access the whole of the information which is shown.

Further, according to another embodiment, the pieces of information obtained on these different representations are crossed, so as to allow the user to easily navigate between the tomosynthesis representation and the double or multi-energy representation, even though these representations are of different natures (one volume and projections).

The coordinates of the regions of interest such as lesions identified on the projections of the double or multi-energy representation are computed for example by using the computing methods used for stereotaxic techniques. The corresponding cut(s) of the tomosynthesis representation is (are) thus identified so that the user may view the corresponding regions of interest thereon.

Conversely, the regions of interest may be identified on the tomosynthesis representation and transferred onto the double or multi-energy representations depending on their positioning and on their dimensions.

The regions of interest may be manually identified by the user on the projections, or detected automatically, or further by a combination of both of these methods such as automatic detection which is corrected and/or validated by the user.

Thus, the user may exploit both morphological information via the tomosynthesis representation and functional information via the double or multi-energy representation.

In another embodiment, the double or multi-energy representation is then the subject of a tomographic reconstruction, for example in order to produce a model of the volume of the contrast product in the subject or organ to be imaged O. This embodiment more particularly consists of applying a tomographic reconstruction to the recombined projections used within the scope of the double or multi energy method.

Figure 4:
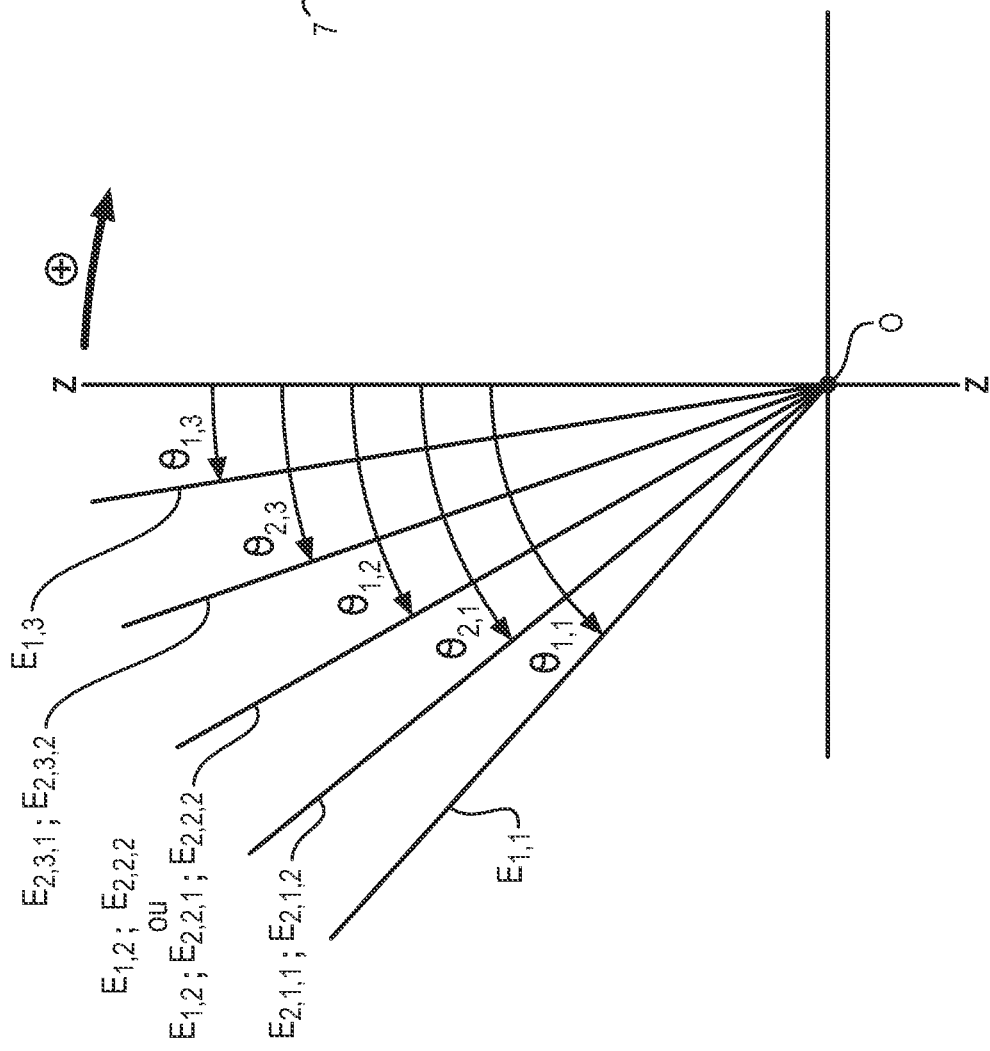
FIG. 4 illustrates a device for applying the method according to according to an embodiment of the present invention.

The method described above is typically applied by a device 1 as illustrated in FIG. 4, the device 1 comprising an X-ray emitting source 3, a receiver 4 positioned facing the source, and a support 6 on which a subject or organ to be imaged O is positioned.

The source 3 is mounted on an actuator 8. The actuator 8 may be a mobile arm adapted for displacing the source 3 with respect to the receiver 4 and adapted for controlling the source for performing the different acquisitions. The receiver 4 may also be mounted on a second actuator configured to vary the orientation of the receiver 4 with respect to the support 6.

The actuator 8 typically comprises additional computing or controlling means.

The device 1 also comprises a computer 7 adapted for performing the operations for processing the acquired images for modeling the subject or the organ to be imaged from the acquired images.

What is claimed is:

1. An imaging method performed by a device comprising an X-ray emitting source, a receiver positioned facing the source, and a support on which a subject or organ to be imaged is positioned, the method comprising:
    defining a first set of orientations of the source and a second set of orientations of the source; and
    acquiring images at the defined orientations of the source, wherein the second set of orientations comprises a number of orientations that is less than the number of orientations of the first set of orientations,
    wherein if the first set of orientations comprises an orientation that the second set of orientations does not comprise, only one image is acquired by X-ray emission at the orientation at acquisition parameters belonging to a first set of acquisition parameters, and if both the first set of orientations and the second set of orientations comprise the same orientation, at least two images are acquired at distinct acquisition parameters at the orientation belonging to a second set of acquisition parameters that is distinct from the first set of acquisition parameters,
    wherein the acquisition of images at each of the orientations of the second set of orientations is performed by X-ray emissions according to several acquisition parameters comprising:
        high energy acquisition parameters belonging to the second set of acquisition parameters in order to obtain high energy images for each of the orientations of the second set of orientations; and
        low acquisition parameters having a maximum energy lower than a maximum energy of the high energy acquisition parameters in order to obtain low energy images, wherein the first set of acquisition parameters comprises the low acquisition parameters for orientations belonging to both the first and to the second set of orientations, and the second set of acquisition parameters comprises the low acquisition parameters for the orientations only belonging to the second set of orientations.

2. The imaging method according to claim 1, the method further comprising:
   treating the images acquired at the first set of orientations so as to produce tomosynthesis models of the subject or organ to be imaged; and
   processing high energy and low energy images acquired so as to produce multi-energy models of the subject or organ to be imaged.

3. The imaging method according to claim 1, wherein acquiring images at the defined orientations of the source comprises performing a single displacement of the source between two extreme orientations, wherein each of the acquisitions at the first set of orientations and at the second set of orientations are performed during the single displacement.

4. The imaging method according to claim 1, wherein acquiring images at the defined orientations of the source comprises:
   performing a displacement of the source between two extreme positions of the first set of orientations, wherein an image is acquired at each of the orientations of the first set of orientations; and
   performing a displacement of the source between two extreme positions of the second set of orientations, wherein at least one image is acquired at each of the orientations of the second set of orientations.

5. The imaging method according to claim 1, wherein at least one of the first and second sets of orientations is symmetrically or asymmetrically distributed with respect to the reference orientation.

6. The imaging method according to claim 1, wherein the acquisition parameters vary depending on the orientation of the source.

7. The imaging method according to claim 1, further comprising injecting a contrast product into the subject or the organ to be imaged.

8. An imaging system comprising:
   an X-ray emitting source;
   a receiver positioned facing the source;
   a support on which a subject or organ to be imaged is positioned; and
   an actuator configured to vary the orientation of the source with respect to the support, to allow displacement of the source according to a first set of orientations and a second set of orientations, and to control the acquisition of images according to distinct energy levels,
   wherein if the first set of orientations comprises an orientation that the second set of orientations does not comprise, only one image is acquired by X-ray emission at the orientation at acquisition parameters belonging to a first set of acquisition parameters, and if both the first set of orientations and the second set of orientations comprise the same orientation, at least two images are acquired at distinct acquisition parameters at the orientation belonging to a second set of acquisition parameters that is distinct from the first set of acquisition parameters,
   wherein the system is configured so that acquisition of images at each of the orientations of the second set of orientations is performed by X-ray emissions according to several acquisition parameters comprising:
      high energy acquisition parameters belonging to the second set of acquisition parameters in order to obtain high energy images for each of the orientations of the second set of orientations; and
      low acquisition parameters having a maximum energy lower than a maximum energy of the high energy acquisition parameters in order to obtain low energy images, wherein the first set of acquisition parameters comprises the low acquisition parameters for orientations belonging to both the first and to the second set of orientations, and the second set of acquisition parameters comprises the low acquisition parameters for the orientations only belonging to the second set of orientations.

9. The system according to claim 8, further comprising a second actuator configured to vary the orientation of the receiver with respect to the support and to allow displacement of the receiver according to the two distinct sets of orientations.

* * * * *